United States Patent [19]

Stoss

[11] 4,417,065
[45] Nov. 22, 1983

[54] PROCESS FOR THE PREPARATION OF ISOSORBIDE 2-NITRATE

[75] Inventor: Peter Stoss, Illertissen, Fed. Rep. of Germany

[73] Assignee: Heinrich Mack Nachf. Chem.-Pharmazeutische Fabrik, Illertissen, Fed. Rep. of Germany

[21] Appl. No.: 381,124

[22] Filed: May 24, 1982

[30] Foreign Application Priority Data

Jun. 22, 1981 [DE]  Fed. Rep. of Germany ....... 3124410

[51] Int. Cl.³ .......................................... C07D 493/04
[52] U.S. Cl. .................................................. 549/464
[58] Field of Search ......................................... 549/464

[56] References Cited

U.S. PATENT DOCUMENTS 4,065,488  12/1977  Chou et al. .......................... 549/464
4,371,703   2/1983  Stoss .................................... 549/464

Primary Examiner—Henry R. Jiles
Assistant Examiner—Bernard Dentz
Attorney, Agent, or Firm—Charles J. Knuth; Peter C. Richardson; Harold W. Ordway

[57] ABSTRACT

A process for the preparation of isosorbide-2-nitrate of the formula

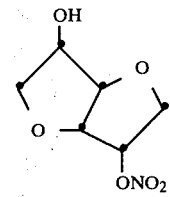

comprising contacting isosorbide with a carboxylic acid anhydride in the presence of a metal salt; esterifying the resultant isosorbide-5-acylate with nitric acid; and converting the resultant isosorbide-5-acylate-2-nitrate to isosorbide-2-nitrate by treatment with an alkyl alcohol in the presence of an alkali metal alcoholate.

9 Claims, No Drawings

PROCESS FOR THE PREPARATION OF ISOSORBIDE 2-NITRATE

BACKGROUND OF THE INVENTION

The use of organic nitrates in coronary diseases belongs today among the generally accepted therapeutic techniques. Originally it was observed that attacks of angina pectoris can be arrested by means of nitroglycerine and subsequently this therapy was extended to preventive treatment. Accordingly, a search has been undertaken for other substances having a similar effect but a longer duration of action. Among the large number of substances synthetized and tested from this point of view, isosorbide dinitrate (ISDN) has proved most acceptable. However, there continues to be a need for nitrates with a longer duration of action.

It has been recognized that the cause of the short half-life of ISDN is the rapid enzymatic biotransformation in the liver. During the metabolic process isosorbide 2-nitrate (2-ISM), isosorbide 5-nitrate (5-ISM), isosorbide (IS) and corresponding conjugates are mainly formed (S. F. Sisenwine and H. W. Ruelius, J. Pharmacol. Exp. Ther. 176:269, 1971).

R. L. Wendt, J. Pharmacol, Exp. Ther. 180:732, 1972 has demonstrated that 2-ISM and 5-ISM have the kind of action that is typical of nitrates. Further studies have show that these metabolites have substantial therapeutic advantages over the parent substance, particularly an improved absorption and thus a greater bioavailability, as well as a distinctly longer half-life. Thus the present use of sustained-action formulations needed to provide a prolonged effect may become superfluous. So far, however, the direct use of the mononitrates, particularly of 2-ISM, is hindered by the painstaking and very expensive synthesis of this compound.

According to I. G. Csizmadia and L. D. Hayward, Photochem. Photobiol. 4:657, 1965, 2-ISM is prepared by partial nitration of isosorbide. However the mixture resulting in this case contains 5-ISM, ISDN and IS with 2-ISM as a minor constituent only. Although 2-ISM can be obtained from this mixture by column chromatography, because of low yields and time-consuming and expensive mode of isolation, this method is of no practical importance.

Another method (M. Anteunis et al., Org. Magnet. Resonance 3:693, 1971) in which IS is converted first into ISDN and the latter is then partially hydrolyzed, also yields the aforementioned mixtures of ISDN, 2-ISM, 5-ISM and IS, whose separation and isolation cannot be carried out in an economically acceptable manner.

In German Offenlegungsschrift No. 2,751,934 and the corresponding U.S. Pat. No. 4,056,488 the following process is described: IS is acylated by means of an acid halide or anhydride, in the presence of an acid catalyst, to a mixture of IS, IS 2-acylate, IS 5-acylate and IS 2,5-diacylate. IS is extracted from this mixture, in order to prevent during the subsequent nitration step, the formation of ISDN which is known to present an explosion hazard. The remaining mixture of IS 2-acylate, IS 5-acylate and IS 2,5-diacylate is esterified with nitric acid, whereby a mixture of IS 2-acylate 5-nitrate, IS 5-acylate 2-nitrate and IS 2,5-diacylate is formed. From this, a mixture of 2-ISM, 5-ISM and IS is obtained by partial hydrolysis. The IS must again be removed by extraction, before the 2-ISM is isolated from the remaining residue by recrystallization from suitable solvents. Even by this method the desired 2-ISM is obtained only in a very moderate yield (24% of the theoretical).

All the aforementioned processes are characterized by the fact that no selective preparation of 2-ISM is possible; rather, mixtures are always obtained which must subsequently be separated into the individual constituents by appropriate separation methods. This mode of operation is painstaking and expensive. In each case it only allows the isolation of 2-ISM in low yields and hence does not permit a commercial preparation.

The first process for a selective preparation of 2-ISM was disclosed in German Offenlegungsschrift No. 2,903,983. In this process isomannide is converted by means of a halide or the anhydride of trifluoromethanesulfonic acid to isomannide 2-trifluoromethanesulfonate. The reaction of this product with an alkali metal nitrate, alkaline-earth nitrate or organic nitrate yields the desired end product under configuration reversal at the 2-carbon atom of the ring system.

Compared with the previously described methods, this process undoubtedly has the advantage of leading to a definite product in a clear sequence of only two reaction steps. However from the standpoint of economy it leaves much to be desired. Thus at the present time isomannide, used as starting product, is much more difficultly accessible and also considerably more expensive than isosorbide. The chemicals needed for the reaction are also decidedly expensive. Finally the overall yield which may be attained according to the indicated examples is only about 13% of the theoretical. Consequently this method likewise is not a suitable industrial process.

Hence there continues to be a need for processes for the preparation of 2-ISM which are based on readily accessible starting products and which provide the desired compound with the use of moderately priced chemicals, and in better yields than is possible according to the prior art.

The subject of the present invention is such an advantageous process for the preparation of isosorbide 2-nitrate.

SUMMARY OF THE INVENTION

As a diol, IS presents two possible sites of attack during acylation. Accordingly, in acylation experiments, mixtures of IS, IS 2-acylate, IS 5-acylate and IS 2,5-diacylate are always obtained. In these cases the composition of the product mixture varies as a function of the method of preparation and the reaction conditions. However, as a rule, the four possible constituents are found to be present in about the same proportions.

The process according to the present invention creates, for the first time, the possibility of directing the acylation of IS toward IS 5-acylate with a high degree of regioselectivity, without the formation of the isomeric IS 2-acylate in significant amounts. This allows preparation of virtually isomer-free 2-ISM in the further course of the reaction, through nitration and transesterification. At the same time pure 2-ISM may be isolated in better yields than hitherto known methods. As a result, for the first time, the preparation of 2-ISM becomes feasible from a commercial point of view.

Thus the present invention is a process for the preparation of 2-ISM, consisting of the following steps:

Acylation of IS, whereby the entry of the acyl group takes place in the 5-position with a high degree of regioselectivity, and virtually isomer-free IS 5-acylate is obtained;

Esterification of this isomer-free IS 5-acylate with nitric acid, with formation of IS 5-acylate 2-nitrate; and Splitting-off of the acyl residue by transesterification.

DETAILED DESCRIPTION OF THE INVENTION

The process according to the invention is carried out as follows:

IS is acylated with 1 to 2 molar equivalents of a carboxylic acid anhydride in the presence of from 0.005 to 0.02 molar equivalents of a catalyst. The acylation takes place either without solvent or in the presence of an inert solvent. Suitable for use as such inert solents are the carboxylic acids containing the corresponding acyl residue, such as acetic acid, propionic acid, butyric acid and the like, and in addition, inert solvents such as chloroform, dichloromethane, acetone, ethyl methyl ketone, dioxane, tetrahydrofuran, acetonitrile, dimethylformamide, dimethylacetamide, dimethyl sulfoxide, ethylene glycol dialkyl ether may be used. The reaction is carried out in a temperature range of from about $-50°$ C. to $+100°$ C., preferably in the range of from $0°$ to $30°$ C., and requires a reaction time of from a few minutes to up to one hundred hours, with 10 to 30 hours being preferred.

Suitable for use as catalysts are salts of metals belonging to Groups 2, 3, 4, 5 and 8 of the periodic system, with the activity within a given group generally increasing from Period 2 to Period 6. Hence the most effective catalysts are to be found mainly in Period 6. The following may be mentioned by way of example: Salts of calcium, strontium, barium, zinc, cadmium, mercury, indium, thallium, the lanthanides, tin, lead, antimony, bismuth, iron, cobalt, nickel. Salts of barium, mercury, lead, and bismuth are peferred. Lead salts are most peferable. The acids used for the formation of the salts can be varied within wide areas and comprise carbonic acid, aliphatic and aromatic carboxylic acids as well as inorganic acids. Preferred metal salts include carbonates, acetates, propionates, benzoates, chlorides, nitrates and phosphates.

Suitable carboxylic acid anhydrides for the above described reaction are striaght-chained and branched aliphatic carboxylic acid anhydrides having from 2 to 6 carbon atoms, preferably acetyl, priopionyl, butyryl, valeryl, caproyl, isobutyryl, isovaleryl and pivaloyl; cycloaliphatic carboxylic acid anhydrides having from 6 to 8 carbon atoms, preferably cyclopentanecarbonyl, cyclohexanecarbonyl and cycloheptanecarbonyl; and aromatic carboxylic acid anhydrides, preferably unsubstituted and substituted benzenecarboxylic acid anhydrides wherein the benzene substituents comprise lower alkyl groups having from 1 to 4 carbon atoms, halogen, methoxy and nitro groups, most preferably benzoyl, o-, m- and p-toluyl, dimethylbenzoyl, trimethylbenzoyl, methoxybenzoyl, nitrobenzoyl and halogenobenzoyl.

The above acylation of IS produces IS 5-acylate with a high degree of regioselectivity and with substantially quantitative conversion. The amount of the isomeric IS 2-acylate thus formed is below the thin-layer-chromatographic limit of detection, and IS 2,5-diacetate is formed in only an insignificant amount. In practice, if the reaction is conducted in the optimum manner, a product of the following composition can be obtained: About 94–96% IS 5-acylate, about 3–6% IS 2,5-diacylate, less than 1% IS; IS 2-acylate is not detectable.

From this crude product IS 5-acylate can, if desired, be obtained with a purity of over 99% by means of appropraite processing and purification methods, such as extraction, distillation or recrystallization. In subsequent reaction of the preparative process it is possible to use, directly, either the pure IS 5-acylate having a purity of more than 99%, or the crude IS 5-acylate obtained during the selective acylation, with a content of about 94–96%, without isolation and purification.

The IS 5-acylate thus obtained is esterified with nitric acid in a known manner to form IS 5-acylate 2-nitrate which is not contaminated by isomeric IS 2-acylate 5-nitrate or by ISDN. Finally, in the last step the 5-acyl group is removed by transesterification in a known manner to form 2-ISM. Preferably the cleavage of the 5-acyl group is obtained by subjecting IS 5-acylate 2-nitrate to transesterification in an alcohol having from 1 to 3 carbon atoms in the presence of an alkali metal alcoholate, in a known manner as for example by the method disclosed in German Auslegeschrift No. 2,903,927. Preferred lower alcohols are methanol or ethanol and preferred alcoholates are sodium or potassium alcoholates having from 1 to 3 carbon atoms.

The reaction may be carried out by isolating the resulting intermediate products and using them in that form for the next step or the isolation of the substances formed in the intermediate stages may be dispensed with, and these substances may be directly subjected to further processing in the form in which they are obtained. This method, involving little technical effort, leads to 2-ISM which, by simple recrystallization of the crude product from a suitable solvent, can be obtained in pure form and in a high yield.

The following examples serve to illustrate the invention.

EXAMPLE 1

A mixture of 146 g of isosorbide, 305 g of p-toluic anhydride and 1 liter of dichloromethane is treated with 5 g of lead acetate and stirred at room temperature for 40 hours. After initial dissolution, the reaction product later precipitates. After cooling to $0°$ C., the crystalline precipitate is filtered by suction and recrystallized from toluene. 210 g of 5-(p-toluyl)-isosorbide are obtained; m.p. $160°–162°$ C.

EXAMPLE 2

A nitrating mixture is prepared from 130 g of 65% nitric acid and 400 ml of acetic anhydride at about $15°$ C. To this mixture are added first 100 ml of dichloromethane and then, in portions, 264 g of 5-(p-toluyl)-isosorbide, during which the temperature is maintained at $10°–15°$ C. Thereupon the mixture is heated to $25°$ C. and allowed to stand at this temperature until a complete conversion can be detected by thin-layer chromatography (about 1 hour). The mixture is treated with 400 ml of dichloromethane and 1 liter of water. The aqueous layer is discarded, the organic phase is thoroughly stirred with dilute aqueous ammonia solution, separated and concentrated in vacuo. The residue is recrystallized from methanol. Yield: 290 g of 5-(p-toluyl)-isosorbide 2-nitrate; m.p. $93°–94°$ C.

EXAMPLE 3

309 g of 5-(p-toluyl)-isosorbide 2-nitrate are suspended in 1 liter of methanol. While stirring, 30% methanolic sodium methylate solution is dropwise added thereto until a distinctly alkaline reaction is obtained, whereby a clear solution results. The mixture is stirred for 2 hours at 40° C., then neutralized with acetic acid and freed from the solvent in vacuo. The residue is distributed at 40° C. between 1 liter of water and 500 ml of petroleium ether, the aqueous phase is separated and concentrated to about 300 ml. On cooling to 0° C., isosorbide 2-nitrate crystallizes out. It is filtered off and washed with 100 ml of cold isopropanol. Yield: 151 g; m.p. 53°–55° C.

EXAMPLE 4

A mixture of 146 g of isosorbide, 150 g of acetic anhydride and 5 g of lead acetate is allowed to stand at room temperature for 20 hours. A nitrating mixture is prepared from 350 ml of acetic anhydride and 130 g of 65% nitric acid while cooling at about 15° C. To this mixture is added the aforementioned acylating mixture, while stirring and cooling to 15° C. Stirring is carried out for an additional 2 hours at room temperature, after which 300 ml of dichloromethane and 1 liter of water are added. The aqueous phase is discarded, the organic phase is washed with dilute aqueous ammonia solution and concentrated in vacuo. The residue is taken up in 200 ml of methanol, treated with 10 ml of 30% methanolic sodium methylate solution and stirred for 1 hour. Thereupon the mixture is neutralized with acetic acid and the solvent removed in vacuo. The residue is dissolved in 200 ml of water under gentle heating (20°–30° C.), the solution is thoroughly stirred with activated carbon, filtered and cooled to 0° C. The isosorbide 2-nitrate which has crystallized out is filtered by suction and washed with 100 ml of ice-cold isopropanol. Yield: 151 g; m.p. 53°–55° C.

EXAMPLE 5

In the same manner as described in Example 4, by acylation of isosorbide with the carboxylic acid anhydrides listed below, the indicated isosorbide-5-acylates are obtained which, without isolation, are likewise esterified with nitric acid and converted, through subsequent transesterification with methanol, into isosorbide 2-nitrate of m.p. 53°–55° C. in comparable yields.

In this procedures, liquid anhydrides are reacted without solvent, and solid anhydrides are dissolved in a suitable solvent such as dichloromethane, tetrahydrofuran, dioxane, acetonitrile or dimethylformamide.

| Anhydride used | Isosorbide 5-acylate |
|---|---|
| Propionic | 5-Propionyl-isosorbide |
| Butyric | 5-Butyryl-isosorbide |
| Valeric | 5-Valeryl-isosorbide |
| Caproic | 5-Caproyl-isosorbide |
| Isobutyric | 5-Isobutyryl-isosorbide |
| Isovaleric | 5-Isovaleryl-isosorbide |
| Pivalic | 5-Pivaloyl-isosorbide |
| Cyclopentanecarboxylic | 5-Cyclopentanecarbonyl-isosorbide |
| Cyclohexanecarboxylic | 5-Cyclohexanecarbonyl-isosorbide |
| Cycloheptanecarboxylic | 5-Cycloheptanecarbonyl-isosorbide |
| Benzoic | 5-Benzoyl-isosorbide |
| o-Toluic | 5-(o-Toluyl)-isosorbide |
| p-Chlorobenzoic | 5-(p-Chlorobenzoyl)-isosorbide |
| m-Methoxybenzoic | 5-(m-Methoxybenzoyl)-isosorbide |
| p-Nitrobenzoic | 5-(p-Nitrobenzoyl)-isosorbide |

I claim:

1. A process for the preparation of isosorbide-2-nitrate of the formula

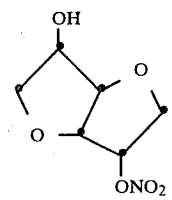

comprising:
- (a) contacting isosorbide with 1 to 2 mole equivalents of carboxylic acid anhydride in the presence of 0.005 to 0.02 mole equivalents of a salt of a metal ion selected from groups 2, 3, 4, 5 or 8 of the periodic system;
- (b) esterifying the resultant isosorbide-5-acylate with nitric acid; and
- (c) converting the resultant isosorbide-5-acylate-2-nitrate to isosorbide-2-nitrate by treatment with an alkyl alcohol having from 1 to 3 carbon atoms in the presence of an alkali metal alcoholate of 1 to 3 carbon atoms.

2. The process of claim 1 wherein said carboxylic acid anhydride is a straight-chained or branch-chained alkyl carboxylic anhydride having from 2 to 6 carbon atoms, cycloalkyl carboxylic anhydride having from 6 to 8 carbon atoms, or unsubstituted or substituted aromatic carboxylic anhydride wherein said substituent is a lower alkyl group having from 1 to 4 carbon atoms, halogen, methoxy or a nitro group.

3. The process of claim 2 wherein said carboxylic acid anhydride is benzoic acid anhydride, toluoyl acid anhydride, dimethyl benzoic acid anhydride, trimethyl benzoic acid anhydride, methoxy benzoic acid anhydride, nitrobenzoic acid anhydride or halo benzoic acid anhydride.

4. The process according to claim 1 wherein said metal salt is a carbonate, chloride, nitrate, phosphate or carboxylate wherein the acyl radical is a straight-chained or branch-chained alkyl having from 2 to 6 carbon atoms, cycloalkyl having from 6 to 8 carbon atoms or optionally substituted phenyl wherein said substituent is methyl, dimethyl, trimethyl, methoxy, nitro or halogen group.

5. The process of claim 4 wherein said metal salt is a carboxylate wherein the acyl radical corresponds to the acyl radical of said carboxylic acid anhydride.

6. The process of claim 4 wherein said metal salt is a calcium, strontium, barium, zinc, cadmium, mercury, indium, thallium, lanthanide, tin, lead, bismuth, antimony, iron, cobalt or nickel salt.

7. The process of claim 6 wherein said metal salt is a lead salt.

8. The process of claim 1 wherein the isosorbide-5-acylate is purified prior to further reaction by means of extraction, distillation or recrystallization.

9. The process according to claim 1 wherein the products obtained in step (a) and/or (b) are further purified prior to subsequent reaction.

* * * * *